(12) United States Patent
Lee et al.

(10) Patent No.: US 10,706,104 B1
(45) Date of Patent: Jul. 7, 2020

(54) SYSTEM AND METHOD FOR GENERATING A GRAPHICAL MODEL

(71) Applicant: Babylon Partners Limited, London (GB)

(72) Inventors: Ciaran M. Lee, London (GB); Anish Dhir, London (GB)

(73) Assignee: Babylon Partners Limited, London (GB)

(*) Notice: Subject to any disclaimer, the term of this patent is extended or adjusted under 35 U.S.C. 154(b) by 0 days.

(21) Appl. No.: 16/522,199

(22) Filed: Jul. 25, 2019

(51) Int. Cl.
  *G06F 16/901* (2019.01)
  *G06F 16/9032* (2019.01)
  *G06F 16/9035* (2019.01)
  *G06F 16/904* (2019.01)

(52) U.S. Cl.
  CPC ........ *G06F 16/9024* (2019.01); *G06F 16/904* (2019.01); *G06F 16/9035* (2019.01); *G06F 16/90332* (2019.01)

(58) Field of Classification Search
  CPC .............. G06F 16/9024; G06F 16/904; G06F 16/90332; G06F 16/9035
  See application file for complete search history.

(56) References Cited

U.S. PATENT DOCUMENTS

| | | | | |
|---|---|---|---|---|
| 2013/0257873 A1* | 10/2013 | Isozaki | ................. | G06T 11/206 345/440 |
| 2014/0351198 A1* | 11/2014 | Isozaki | ................. | G06N 7/005 706/54 |
| 2016/0267224 A1* | 9/2016 | Natarajan | .......... | G06Q 10/0635 |
| 2016/0292248 A1* | 10/2016 | Garcia | ................. | G06Q 10/063 |

OTHER PUBLICATIONS

Tillman, R., et al., "Learning equivalence classes for acrylic models with latent and selection variables from multiple datasets with overlapping variables," in Proceedings of the Fourteenth International Conference on Artificial Intelligence and Statistics, p. 3-15, 2011.

(Continued)

*Primary Examiner* — Jay A Morrison
(74) *Attorney, Agent, or Firm* — McDermott Will & Emery LLP

(57) ABSTRACT

Methods for creating a model that is a graphical representation are provided. In one aspect, a method includes including receiving a first dataset including a first variable and a third variable, and a second dataset including a second variable and the third variable. The method also includes creating graphical representations of the first and second datasets by applying conditional independence tests on them, and storing conditional independence information obtained by applying the conditional independence tests on the first and second datasets. The method also includes applying a bivariate causal discovery algorithm. The method further includes modifying the graphical representations of the first and second dataset according to the determined causal relations, and creating a set of candidate graphical representations for a third dataset including the first and second datasets. Each candidate graphical representation is consistent with the conditional independence information. Systems and machine-readable media are also provided.

13 Claims, 14 Drawing Sheets

(56) References Cited

OTHER PUBLICATIONS

Zhang, J., "A characterization of markov equivalence classes for directed acyclic graphs with latent variables," in Proceedings of the Twenty-Third Conference on Uncertainty in Artificial Intelligence, UAI'07, (Arlington, VA, United States), pp. 450-457, AUAI Press 2017).
Hoyer, P. ., et al., Nonlinear causal discovery with additive noise models. Neural Information Processing Systems Foundation, 2009.
Shimizu, S., et al., "A linear non-gaussian acyclic model for causal discovery," Journal of Machine Learning Research, vol. 7, no. Oct, pp. 2003-2030, 2006.
Janzing, D., et al., "Information-geometric approach to inferring causal directions," Artificial Intelligence, vol. 182, pp. 1-31, 2012.
Mitrovic, J., et al., "Causal inference via kernel deviance measures," in Advances in Neural Information Processing Systems, pp. 6986-6994, 2018.
Janzing, D., et al., Identifying counfounders using additive noise models. arXiv:1205.2640v1[stat.ML], 2012.
Goudet, O., et al., "Learning functional causal models with generative neural networks," in Explainable and Interpretable Models in Computer Vision and Machine Learning, pp. 39-80, Springer, 2018.
Zhang, K., et al., "On the identifiability of the post-nonlinear causal model," in Proceedings of the 25 conference on uncertainty in artificial intelligence, pp. 647-655, 2009.
Fonollosa, J. A., "Conditional distribution variability measures for causality detection," arXiv preprint arXiv:1601.06680, 2016.
Lopez-Paz, D., "Towards a learning theory of cause-effect inference," ICML, 1452-1461, 2015.
Lee, C. M., et al., "Causal inference via algebraic geometry: feasibility tests for functional causal structures with two binary observed variables," Journal of Causal Inference, vol. 5, No. 2, 2017.
Wolfe, E., et al., "The inflation technique for causal inference with latent variables," arXiv preprint arXiv:1609.00672, 2016.
Gasse, M., et al., "An experimental comparison of hybrid algorithms for bayesian network structure learning," in Joint European Conference on Machine Learning and Knowledge Discovery in Databases, pp. 58-73, Springer, 2012.
Tsamardinos, I., et al., "The max-min hill-climbing bayesian network structure learning algorithm," Machine learning, vol. 65, No. 1, pp. 31-78, 2006.
Pearl, J., Causality (2nd edition). Cambridge University Press, 2009.
Spirtes, P., et al., Causation, Prediction, and Search. Adaptive computation and machine learning, The MIT press, 2nd edition, 2000.
Kalainathan, D., et al., "Sam: Structural agnostic model, causal discovery and penalized adversarial learning," arXiv preprint arXiv:1803.04929, 2018.
Danks, D., "Integrating locally learned causal structures with overlapping variables," in Advances in Neural Information Processing Systems, pp. 1665-1672, 2009.
Tillman, R., et al., "Learning equivalence classes of acyclic models with latent and selection variables from multiple datasets with overlapping variables," in Proceedings of the Fourteenth International Conference on Artificial Intelligence and Statistics, pp. 3-15, 2011.
Zhang, K., et al., "Kernel-based conditional independence test and application in causal discovery," arXiv preprint arXiv:1202.3775, 2012.
Friedman, N., et al., "Bayesian network classifiers," Machine learning, vol. 29, No. 2-3, pp. 131-163, 1997.
Daniusis, P., et al., "Inferring deterministic causal relations," arXiv preprint arXiv:1203.3475, 2012.
Tsamardinos, I., et al., "Towards integrative causal analysis of heterogeneous data sets and studies," Journal of Machine Learning Research, vol. 13, no. Apr, pp. 1097-1157, 2012.
Triantafillou, S., et al., "Constraint-based causal discovery from multiple interventions over overlapping variable sets.," Journal of Machine Learning Research, vol. 16, pp. 2147-2205, 2015.
Sajja, S., et al., "Bayesian network structure learning with messy inputs: the case of multiple incomplete datasets and expert opinions," in International Conference on Algorithmic DecisionTheory, pp. 123-138, Springer, 2015.
Claassen, T., et al., "Causal discovery in multiple models from different experiments," in Advances in Neural Information Processing Systems, pp. 415-423, 2010.
Janzing, D., "Merging joint distributions via causal model classes with low vc dimension," arXiv preprint arXiv:1804.03206, 2018.
Triantafillou, S., et al., "Learning causal structure from overlapping variable sets," in Proceedings of the Thirteenth International Conference on Artificial Intelligence and Statistics, pp. 860-867, 2010.
Janzing, D., et al., "Detecting confounding in multivariate linear models via spectral analysis," Journal of Causal Inference, vol. 6, Issue 1, 2018.
Hoyer, P.O., et al., "Estimation of causal effects using linear non-gaussian causal models with hidden variables," International Journal of Approximate Reasoning, vol. 49, No. 2, pp. 362-378, 2008.
Sachs, K., et al., "Causal protein-signaling networks derived from multiparameter single-cell data.," Science (New York, NY), vol. 308, No. 5721, p. 523, 2005.
Zhang, J., "A characterization of markov equivalence classes for directed acyclic graphs with latent variables," in Proceedings of the Twenty-Third Conference on Uncertainty in Artificial Intelligence, UAI'07, (Arlington, Virginia, United States), pp. 450-457, AUAI Press, 2007.
Spirtes, P., et al., "Causal inference in the presence of latent variables and selection bias," in Proceedings of the Eleventh conference on Uncertainty in artificial intelligence, pp. 499-506, Morgan Kaufmann Publishers Inc., 1995.
Fisher, R.A., "Statistical methods for research workers," in Breakthroughs in statistics, pp. 66-70, Springer, 1992.
Zhang, J., et al., "Discussion of "learning equivalence classes of acyclic models with latent and selection variables from multiple datasets with overlapping variables"," in Proceedings of the Fourteenth International Conference on Artificial Intelligence and Statistics, pp. 16-18, 2011.
Mitrovic, J., et al., "Causal inference via kernel deviance measures," in Advances in Neural Information Processing Systems 31 (S. Bengio, H. Wallach, H. Larochelle, K. Grauman, N. Cesa-Bianchi, and R. Garnett, eds.), pp. 6986-6994, Curran Associates, Inc., 2018.
Melancon, G., et al., "Random generation of dags for graph drawing," 2000.
Lee, C.M., et al., "Towards device-independent information processing on general quantum networks," Physical Review Letters, vol. 120, No. 2, p. 020504, 2018.
Allen, J.M.A., et al., "Quantum common causes and quantum causal models," Physical Review X, vol. 7, No. 3, p. 031021, 2017.
Lee, C.M., "Device-independent certification of non-classical measurements via causal models," arXiv preprint arXiv:1806.10895, 2018.
Chaves, R., et al., "Information—theoretic implications of quantum causal structures," Nature communications, vol. 6, p. 5766, 2015.
Spirtes, P., et al., Automated Search for Causal Relations: Theory and Practice, Carnegie Mellon University, Chapter 27, 2010.
Pearl, J., "Theoretical Impediments to Machine Learning With Seven Sparks from the Causal Revolution," arXiv:1801.04016 2018.

* cited by examiner

| Table 1: Results | | Number of PAGs | Number of MAGs |
|---|---|---|---|
| Synthetic 1 | IOD | 12 | 42 |
| | Method 2 | 4 | 7 |
| | Method 1 | 1 | 1 |
| Synthetic 2 | IOD | -- | -- |
| | Method 2 | 28 | 88 |
| | Method 1 | 1 | 1 |
| Protein | IOD | -- | -- |
| | Method 2 | 208 | 626 |
| | Method 1 | 41 | 41 |
| Cancer | IOD | 12 | 42 |
| | Method 2 | 6 | 6 |
| | Method 1 | 6 | 6 |

Fig. 12

SYSTEM AND METHOD FOR GENERATING A GRAPHICAL MODEL

FIELD

Embodiments described herein relate to systems and methods for generating a graphical model.

BACKGROUND

Causal knowledge is fundamental to many domains of science, medicine and economics. This is due to the fact that causal relations, unlike correlations, allow one to reason counterfactually and to analyse the consequences of interventions. While powerful approaches to discovering causal relations between multiple variables in the absence of randomised controlled trials have been developed, many of these require all variables to be jointly measured and recorded in a single dataset. In many domains this assumption does not hold, due to ethical concerns, or financial and technological constraints.

For instance, in certain countries medical variables could be censored differently, meaning there is only access to joint measurements of certain variables, wherein joint measurements refer to measurements recorded at the same time. In another example, distinct medical sensors may measure differently, but overlapping aspects of a particular disease or physiological function. In another example, countries may report country-specific economic variables as well as those reported by other nations, due to specific financial reporting practices. In these examples, multiple datasets are provided, each recording a potentially different, but overlapping, set of variables.

Arrangements of the present invention will be understood and appreciated fully from the following detailed description, made by way of example only and taken in conjunction with drawings in which:

FIG. 12 shows a table of results; and

Figure 14:
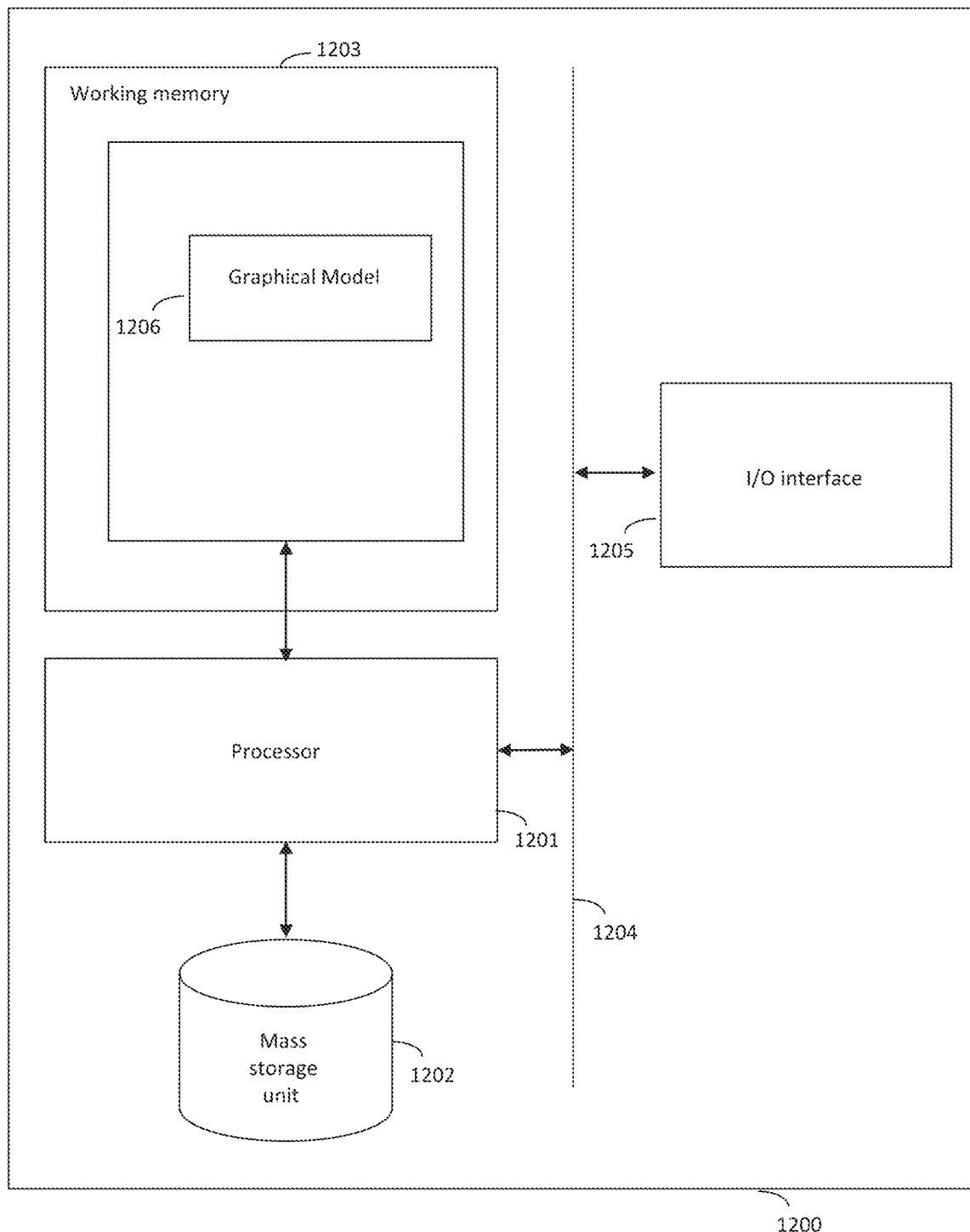

FIG. 14 a schematic of a system in accordance with an embodiment.

DETAILED DESCRIPTION

In an embodiment, a computer implemented method of creating a model that is a graphical representation is provided, the model comprising: receiving, a first dataset comprising a first variable and a third variable and a second dataset comprising a second variable and the third variable; creating graphical representations of the first dataset and the second dataset by applying conditional independence tests on the first dataset and second dataset; storing conditional independence information obtained by applying the conditional independence tests on the first dataset and the second dataset; applying a bivariate causal discovery algorithm to determine a causal relation between the first and third variable in the first dataset and a causal relation between the second and third variable in the second dataset, the causal discovery algorithm being able to determine if the first variable causes the third variable, the third variable causes the first variable, the second variable causes the third variable and the third variable causes the second variable; modifying the graphical representations of the first and second dataset according to the determined causal relations; and creating a set of candidate graphical representations for a third dataset comprising the first dataset and the second dataset, wherein each candidate graphical representation is consistent with the conditional independence information.

This method provides for the generation of a model using overlapping datasets, wherein the model relates variables that may not have been measured at the same time. These models enable the provision of improved computer-implemented diagnosis or triage. This method results in a smaller set of graphical representations for the union of datasets than using other methods. Thus, it provides an improved method of determining the true graphical model relating overlapping datasets, as the true graphical model is contained within the set of consistent graphical representations.

In one embodiment, the bivariate causal discovery algorithm is causally sufficient, and the method further comprising: storing causal relation information between pairs of variables, the causal relation information obtained by applying the bivariate causal discovery algorithm; checking each candidate graphical representation for consistency with the causal relation information using a set of criterion; and outputting a set of consistent graphical representations comprising candidate graphical representations that are consistent with the causal relation information.

This method results in a yet smaller set of graphical representations for the union of datasets than using other methods. Thus, it provides an improved method of determining the true graphical model relating overlapping datasets, as the true graphical model is contained within the set of consistent graphical representations.

In a further embodiment, the set of criterion distinguishes between possible causal structures between two variables in each candidate graphical representation. In a yet further embodiment, checking each candidate's graphical representation for consistency with the causal relation information using a set of criterion comprises: applying the criterion to the candidate's graphical representation to identify a causal structure between two variables and checking if the causal structure is consistent for the causal relation information for two variables.

In an embodiment, the set of criterion encodes conditional independence information between variables in a causal structure.

In a further embodiment, the causal relation information is stored in three data structures depending on whether the relation between two variables is directed, comprises a common latent variable or has both a directed relation and a common latent variable.

In an embodiment, if the relation between the variables is a directed relation, the variables are stored in the data structure in an order that reflects the direction of the relation.

In an embodiment, the set of consistent graphical representations comprises maximal ancestral graphs.

In a further embodiment, if every maximal ancestral graph of a partial ancestral graph is consistent, the set of consistent graphical representations comprises the partial ancestral graph.

In an embodiment, there is a non-transitory carrier medium carrying computer readable instructions being adapted to cause a computer to run the method recited above.

In an embodiment, a computer-implemented method of determining a response to a user inputted query, using a model, the method comprising: receiving a user inputted query; identifying a node in said model related to said query, said model being stored in a memory of a computer and performing inference on said model to provide a response to said user, wherein, said model is constructed by the method of described above.

In another embodiment, a system adapted to generate a model that is a graphical representation is provided, the system comprising a processor and a memory, the processor being adapted to: receive a first dataset comprising a first variable and a third variable and a second dataset comprising a second variable and the third variable; create graphical representations of the first dataset and the second dataset by applying conditional independence tests on the first dataset and second dataset; store conditional independence information obtained by applying the conditional independence tests on the first dataset and the second dataset; apply a bivariate causal discovery algorithm to determine a causal relation between the first and third variable in the first dataset and a causal relation between the second and third variable in the second dataset, the causal discovery algorithm being able to determine if the first variable causes the third variable, the third variable causes the first variable, the second variable causes the third variable and the third variable causes the second variable; modify the graphical representations of the first and second dataset according to the determined causal relations; and create a set of candidate graphical representations for a third dataset comprising the first dataset and the second dataset, wherein each candidate graphical representation is consistent with the conditional independence information.

In a further embodiment, the bivariate causal discovery algorithm is causally sufficient, the processor being further adapted to: store causal relation information between pairs of variables, the causal relation information obtained by applying the bivariate causal discovery algorithm; check each candidate's graphical representation for consistency with the causal relation information using a set of criterion and output a set of consistent graphical representations comprising candidate graphical representations that are consistent with the causal relation information.

The disclosed system and method provides an improvement to computer-implemented diagnosis or triage. Specifically, the disclosed system and method provides for the generation of a model using overlapping datasets, wherein the model relates variables that may not have been measured at the same time. These models enable the provision of improved computer-implemented diagnosis or triage.

Figure 1:
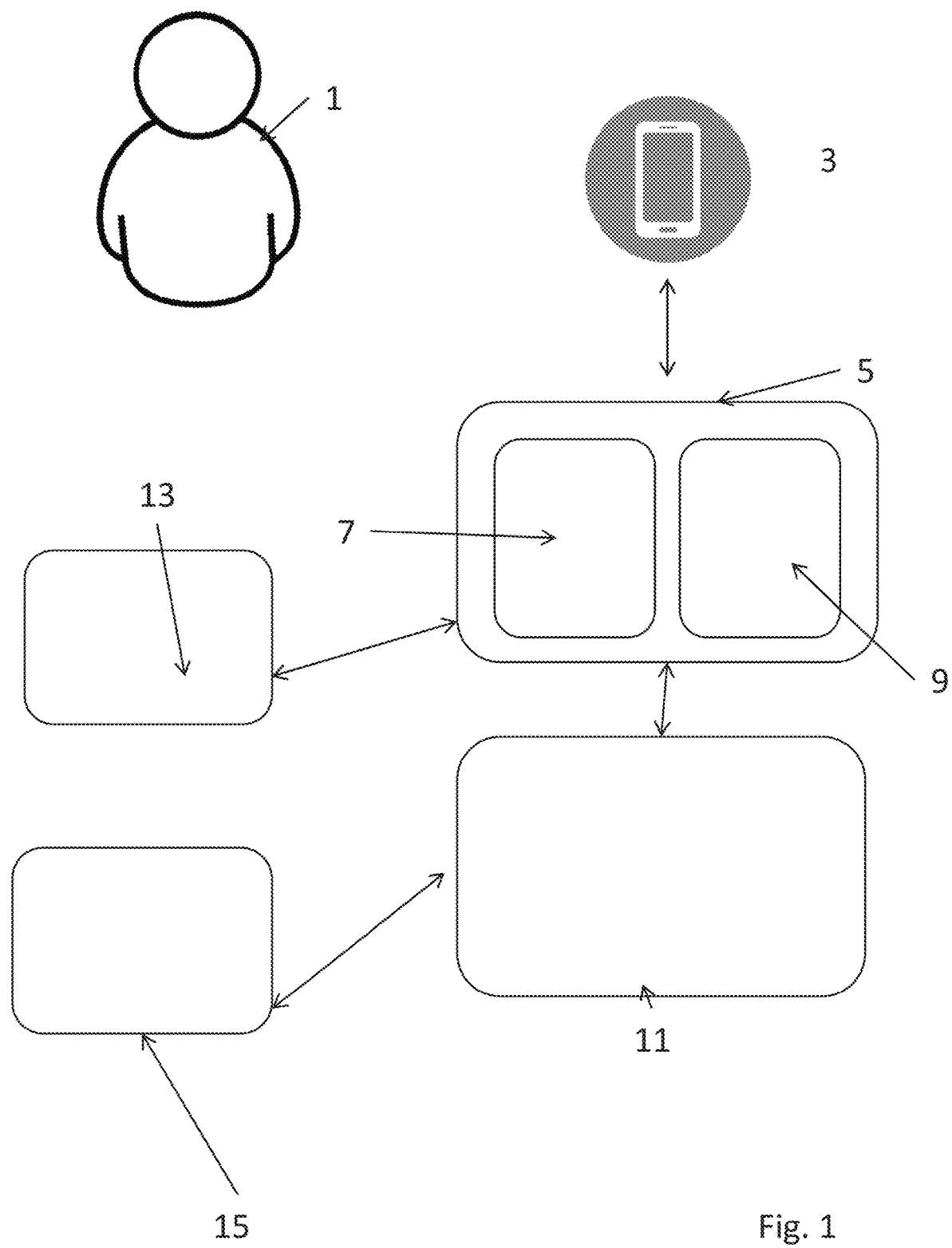
FIG. 1 is a schematic of a system in accordance with an embodiment.

FIG. 1 is a schematic of a diagnostic system. In one embodiment, a user 1 communicates with the system via a mobile phone 3. However, any device could be used, which is capable of communicating information over a computer network, for example, a laptop, tablet computer, information point, and fixed computer, etc.

The mobile phone 3 will communicate with interface 5. Interface 5 has 2 primary functions, the first function 7 is to take the words uttered by the user and turn them into a form that can be understood by the inference engine 11. The second function 9 is to take the output of the inference engine 11 and to send this back to the user's mobile phone 3.

In some embodiments, Natural Language Processing (NLP) is used in interface 5. NLP helps computers interpret, understand and then use everyday human language and language patterns. It breaks both speech and text down into shorter components and interprets these more manageable blocks to understand what each individual component means and how it contributes to the overall meaning, linking the occurrence of medical terms to the Knowledge Graph. Through NLP it is possible to transcribe consultations, summarise clinical records and chat with users in a more natural, human way.

However, simply understanding how users express their symptoms and risk factors is not enough to identify and provide reasons about the underlying set of diseases. For this, the inference engine 11 is used. The inference engine is a powerful set of machine learning systems, capable of reasoning on a space of >100s of billions of combinations of symptoms, diseases and risk factors, per second, to suggest possible underlying conditions. The inference engine can provide reasoning efficiently, at scale, to bring healthcare to millions.

In an embodiment, the Knowledge Graph 13 is a large structured medical knowledge base. It captures human knowledge on modern medicine encoded for machines. This is used to allow the above components to speak to each other. The Knowledge Graph keeps track of the meaning behind medical terminology across different medical systems and different languages.

In an embodiment, the patient data is stored using a so-called user graph 15.

Figure 2:
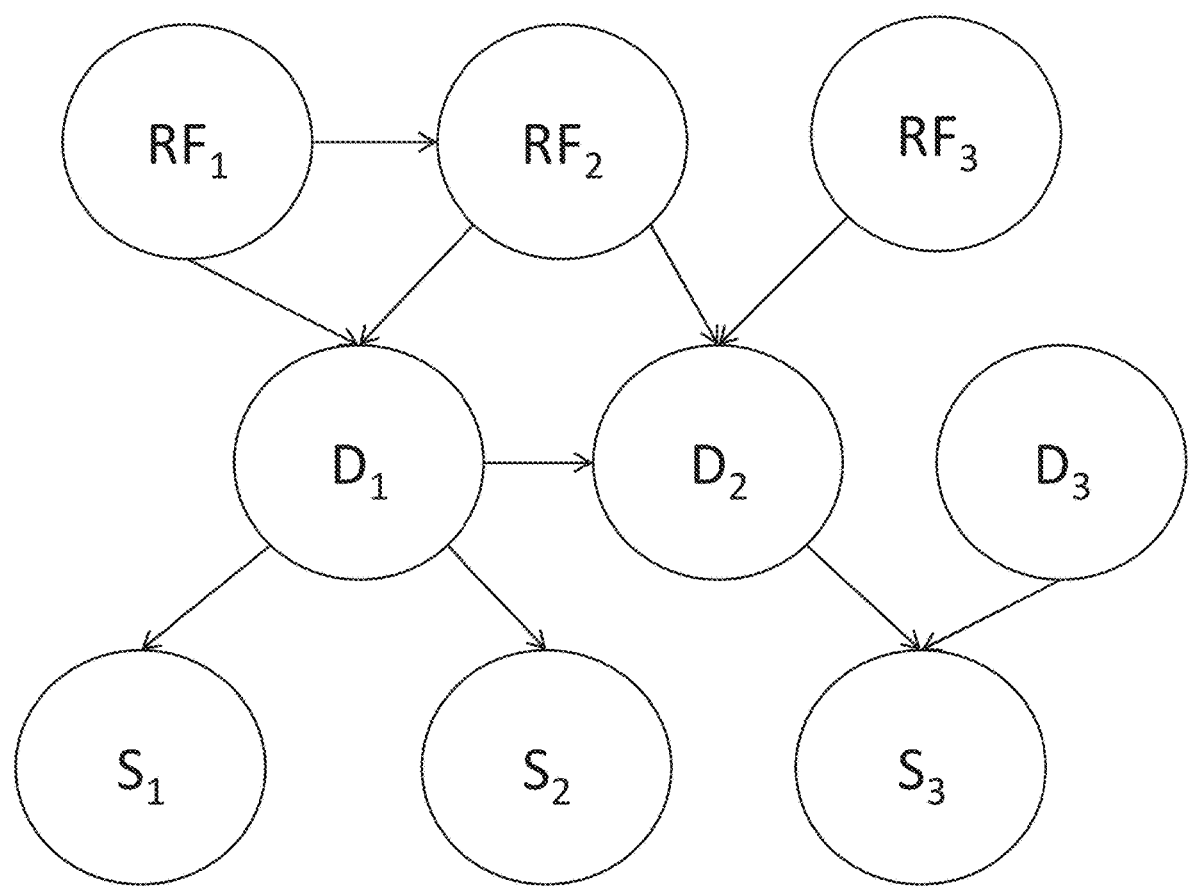
FIG. 2 is a diagram of a probabilistic graphical model of the type that can be used with the system of FIG. 1.

FIG. 2 is a depiction of a graphical model of the type used in the system of FIG. 1.

The graphical model provides a natural framework for expressing probabilistic relationships between random variables, to facilitate causal modelling and decision making. In the model of FIG. 2, when applied to diagnosis, D stands for diagnosis, S for symptom and RF for Risk Factor. Three layers: risk factors, diseases and symptoms. Risk factors causes (with some probability) influence other risk factors and diseases, diseases causes (again, with some probability) other diseases and symptoms. There are prior probabilities and conditional marginals that describe the "strength" (probability) of connections.

In this simplified specific example, the model is used in the field of diagnosis. In the first layer, there are three nodes $S_1$, $S_2$ and $S_3$, in the second layer there are three nodes $D_1$, $D_2$ and $D_3$ and in the third layer, there are two nodes $RF_1$, $RF_2$ and $RF_3$.

In the graphical model of FIG. 2, each arrow indicates a dependency. For example, $D_1$ depends on $RF_1$ and $RF_2$. $D_2$ depends on $RF_2$, $RF_3$ and $D_1$. Further relationships are possible. In the graphical model shown, each node is only dependent on a node or nodes from a different layer. However, nodes may be dependent on other nodes within the same layer.

To create a relevant graphical model from datasets each recording a potentially different, but overlapping, set of variables, datasets must be collated and combined in such a way that causal relations between non-overlapping variables—which have never been jointly measured—can be discovered. For example, in the creation of the model of FIG. 2, a first dataset ($D_1$, $RF_2$) and a second dataset ($D_2$, $RF_2$) may be provided, where the datasets overlap in $RF_2$. It is desirable to perform data fusion of these datasets to discover a causal relationship between $D_1$ and $D_2$.

Background Information on PGMs

Figure 3A:
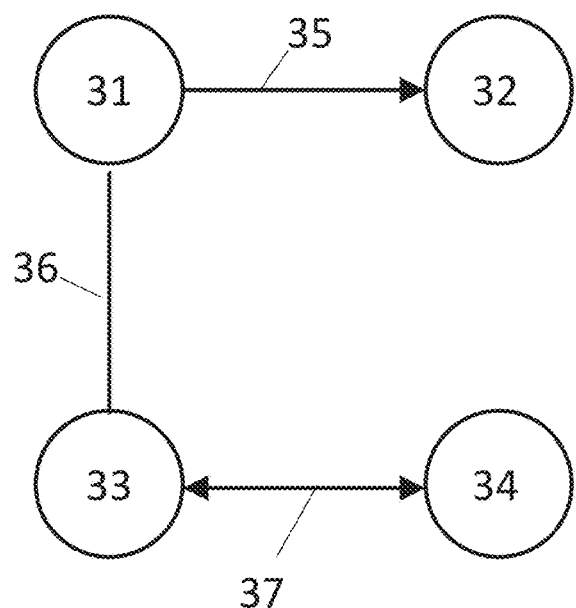
FIG. 3(a) is an example of a mixed graph with directed and undirected edges

To facilitate an understanding, some background information on probabilistic graphical models (PGMs) will be given:

A mixed graph $\mathcal{G} = \langle \mathcal{V}, \mathcal{E} \rangle$, with vertices $\mathcal{V}$ and edges $\mathcal{E}$, is defined as a graph containing three types of edges: directed →, undirected – and bidirected ↔. If two nodes share an edge, they are adjacent. FIG. 3(a) shows an example of a mixed graph 30. The mixed graph 30 has vertices (or nodes) 31, 32, 33 and 34, and edges 35, 36, 37 and 38. Edge 35 is a directed edge. Edge 37 is a bidirected edge. Edges 36 and 38 are undirected edges. Nodes 31 and 32 are adjacent as they share the edge 35. Nodes 31 and 34 are not adjacent, as they do not share an edge.

A path is then defined as a sequence of nodes $\langle V_1 \ldots V_i \ldots V_n \rangle$ such that $V_i$ and $V_{i+1}$ are adjacent for all i and no node is repeated in the sequence. A path is directed if it follows the direction of the arrows. Node X is an ancestor of a node Y if there exists a directed path from X to Y. Node Y is then referred to as a descendent of node X. An ancestor is a parent if there are no intermediate nodes in the path, the direct descendent is then a child. In a graph $\mathcal{G}$ the ancestors of X are denoted as $\mathbf{Anc}_\mathcal{G}^X$ and descendants are denoted as $\mathbf{Des}_\mathcal{G}^X$.

A path is a collider $\langle V_{i-1}, V_i, V_{i+1} \rangle$ if $V_{i-1}$ and $V_{i+1}$ both have a directed edge pointed at $V_i$. A collider is then an immorality if $V_{i-1}$ and $V_{i+1}$ are not adjacent. A path between X, Y is active with respect to a set of nodes Z in a graph $\mathcal{G}$ with $\{X, Y\} \notin Z$, if: (1) $\langle V_{i-1}, V_i, V_{i+1} \rangle$ is a collider in the path, then $\{\{V_i\} \cup \mathbf{Des}_\mathcal{G}^{V_i}\} \cap Z \neq 0$, and (2) if $V_i \in Z$ then $\langle V_{i-1}, V_i, V_{i+1} \rangle$ is a collider.

Figure 3B:
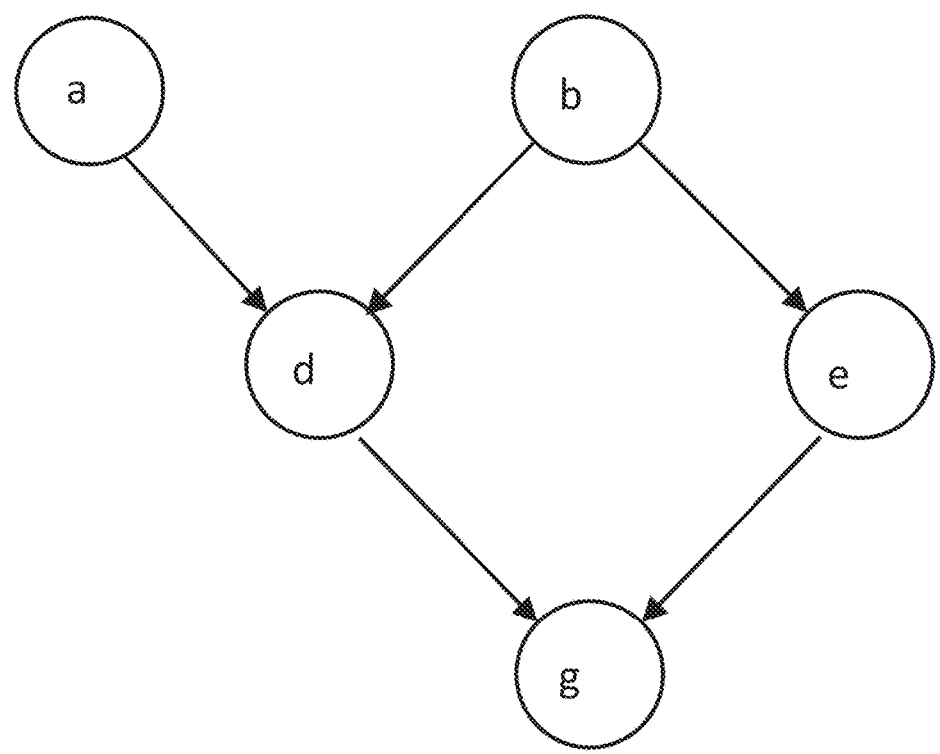
FIG. 3(b) is an example of a graph with m-separated nodes.

In a graph $\mathcal{G}$, two nodes are m-separated given Z if there does not exist an active path between them with respect to Z, denoted as $\mathbf{msep}_\mathcal{G}(X, Y|Z)$. Referring to FIG. 3(b), there does not exist an active path between a to g that does not include the nodes d and e. Therefore nodes a and g are m-separated with respect to the set of nodes d and e.

Closely related to the concept of m-separation is the graph concept of inducing paths. An inducing path between nodes X, Y relative to Z in a graph $\mathcal{G}$ is a path $\langle X \ldots V_i \ldots Y \rangle$ such that: (1) If $V_i \notin Z$ then $\langle V_{i-1}, V_i, V_{i+1} \rangle$ is a collider, and (2) If $\langle V_{i-1}, V_i, V_{i+1} \rangle$ is a collider, then $V_i \in \mathbf{Anc}_\mathcal{G}^X \cup \mathbf{Anc}_\mathcal{G}^Y$. If there is an inducing path between two nodes, they cannot be m-separated.

A maximal ancestral graph (MAG) $\mathcal{G} = \langle \mathcal{V}, \mathcal{E} \rangle$ is a mixed graph that is: (1) ancestral: the graph is acyclic and does not have any arrows pointing into nodes with an undirected edge (X-Y) and (2) maximal: for any distinct nodes $V_i$, $V_j \in \mathcal{V}$, if $V_i$, $V_j$ are not adjacent in $\mathcal{G}$, then $\mathcal{G}$ does not contain any inducing paths between them with respect to the empty set. A directed acyclic graph (DAG) is just a MAG with directed edges. In addition to the independences encoded by a DAG, MAGs allow for the encoding of latent variables that may be confounders—using a bidirected edge or selection variables—using an undirected edge.

It is assumed in the rest of this work that the faithfulness assumption holds. That is, a MAG encodes an m-separation $\mathbf{msep}_\mathcal{G}(X,Y|Z)$ if only there exists a probability distribution on $\mathcal{G}$, $\mathbb{P}_\mathcal{G}$, in which X is independent of Y given Z, denoted $X \perp\!\!\!\perp Y | Z$. There will usually be more than one MAG that can encode the same conditional independence information of a distribution $\mathbb{P}$. Such MAGs are said to be Markov equivalent and belong to the same Markov equivalence class.

Two MAGs, $\mathcal{G} = \langle \mathcal{V}, \mathcal{E} \rangle$, and $\mathcal{H} = \langle \mathcal{W}, \mathcal{F} \rangle$ are Markov equivalent if they contain the same adjacencies, immoralities and discriminating paths. If $\mathcal{W} \subset \mathcal{G}$, $\mathcal{H}$ is said to be a marginal of $\mathcal{G}$ if the following holds for every $X, Y \in \mathcal{W}$: (1) if nodes X and Y are adjacent in $\mathcal{H}$, then they must have an inducing path in $\mathcal{G}$ with respect to $\mathcal{V} \setminus \mathcal{W}$ and (2) for every Z that m-separates X and Y in $\mathcal{H}$, X and Y are also m-separated by Z in $\mathcal{G}$.

The Partial Ancestral Graph (PAG) convention for the graphical representation of Markov equivalent MAGs is followed. Here, an edge type is considered invariant if all the MAGs in the Markov equivalent class have the same edge. An arrowhead and tail are only represented in the PAG graph if they are invariant in the entire class. The rest of the edges are represented by a circle ° symbolising that there are at least two MAGs in the Markov equivalence class with different edge types between the same variables.

Discovering Causal Structure from a Single Dataset

Methods for discovering causal structure from a single independent and identically distributed (i.i.d.) dataset largely fall into two categories. The first is global causal discovery, which aims to learn a partially undirected version of the underlying DAG. There are two distinct approaches to this: constraint and score based. The constraint-based approach uses conditional independence tests to determine which variables should share an edge in the causal structure. Examples include the PC, IC and FCI algorithms. There are also examples employing kernel-based conditional independence tests. The score-based approach utilizes a scoring function, such as Minimum Description Length, to evaluate each network with respect to some training data and searches for the optimal network according to this function. Hybrids employing both constraint and score-based methods appear to outperform either approach alone.

Bivariate Causal Discovery on a Single Dataset

The main limitation of global discovery algorithms is that they cannot always orient edges between dependent variables. That is, they can only learn causal structure up to a Markov equivalence class. In particular, they cannot distinguish any of the structures in FIG. 4(a) to FIG. 4(e). FIG. 4(a) to FIG. 4(e) show all causal structures between two correlated variables where solid nodes indicate observed variables and dashed nodes indicate latent variables.

The second category of causal discovery algorithm, termed bivariate causal discovery (BCD), aims to overcome this issue by specifying some assumptions which—if satisfied—make the intuitive asymmetry between cause and effect manifest at an observational level. Examples include the Linear Non-Gaussian AdditiveModel (LiNGAM), the Additive Noise Model (ANM), the information geometric causal discovery algorithm, and the kernel conditional deviance causal discovery (KCDC) algorithm, amongst others.

Discovering Causal Structure from Multiple Overlapping Datasets

The first algorithm for learning causal structure from overlapping datasets was integration of overlapping networks (ION). This was extended and improved upon by the integration of overlapping datasets (IOD) algorithm.

The authors of IOD employed conditional independence tests to teach the Markov equivalence class each individual dataset belongs to, and then determined the equivalence classes of consistent joint structures among all variables in the union of datasets. Here, a "consistent\" joint structure is one whose conditional independences don't contradict those already taught from each individual dataset.

Approaches based on conditional independence tests are limited as they can only determine causal structure up to Markov equivalence class. They fail to distinguish multiple causal structures between small numbers of variables, such as those depicted in FIG. 4(a) to FIG. 4(c). As many medical studies individually measure relatively small numbers of variables, this is a major roadblock to extracting useful causal information. Moreover, conditional independence approaches appear to struggle when the number of overlapping variables is small. Fortunately, the last decade has seen the development of elegant algorithms for discovering causal relations, which go beyond conditional independence and can distinguish different members of the same Markov equivalence class—assuming all variables have been jointly measured. These algorithms, termed bivariate causal discovery, employ tools from machine learning and assumptions about what it means for one variable to cause another, allowing for a more fine-grained approach to discovering causal relations.

Bivariate Causal Discovery

In an embodiment, bivariate causal discovery algorithms are applied to the problem of learning consistent causal structures from overlapping datasets.

The following example illustrates the power of bivariate causal discovery to learn consistent causal structures from overlapping datasets.

Consider two datasets, $\{X, Y\}$ and $\{Y, Z\}$. The aim is to learn all consistent joint causal structures involving these three variables. In this example, it is assumed there is access to a causally sufficient bivariate causal discovery algorithm that can distinguish all the causal structures depicted in FIG. 4(a) to FIG. 4(e). That is, when the causal discovery algorithm is fed samples of X, Y and Y, Z, it outputs the correct causal structure from all the possibilities depicted in FIG. 4(a) to FIG. 4(e).

One way such causal sufficiency could hold is if it is promised that the data satisfies the identifiability requirements of the causal discovery algorithm under consideration. For instance, if LiNGAM is employed then every observed variable would need to depend linearly on its parents and a latent, independent noise term, with the noise term distributed in a non-Gaussian manner.

Figure 4A:
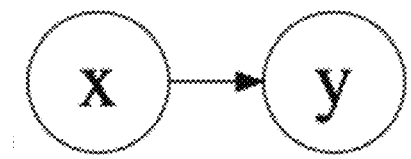
FIG. 4(a) is a possible causal structure between two correlated variables, solid nodes indicate observed variables and dashed nodes indicate latent variables.

Suppose that using this algorithm it is found that X←Y, that is Y causes X, and Y↔Z, that is Y and Z share a latent common cause, as illustrated in FIG. 4(a). As X and Z have never been jointly measured and could each have been measured under different conditions, causal discovery cannot be used on them.

However, a causal structure between them can be posited and then checked if this structure is consistent with the causal information extracted from the individual datasets.

Figure 4B:
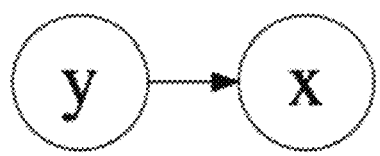
FIG. 4(b) is a possible causal structure between two correlated variables, solid nodes indicate observed variables and dashed nodes indicate latent variables.
Figure 4D:
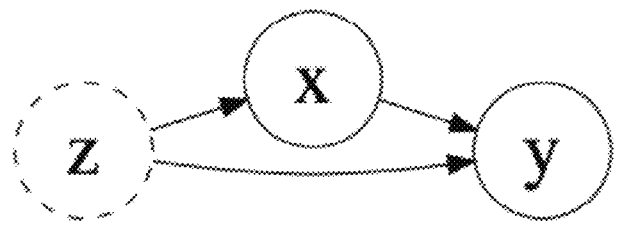
FIG. 4(d) is a possible causal structure between two correlated variables, solid nodes indicate observed variables and dashed nodes indicate latent variables.
Figure 4E:
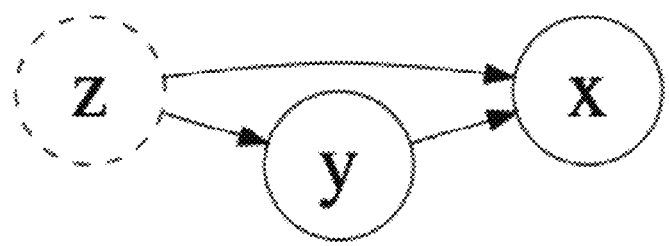
FIG. 4(e) is a possible causal structure between two correlated variables, solid nodes indicate observed variables and dashed nodes indicate latent variables.
Figure 5A:
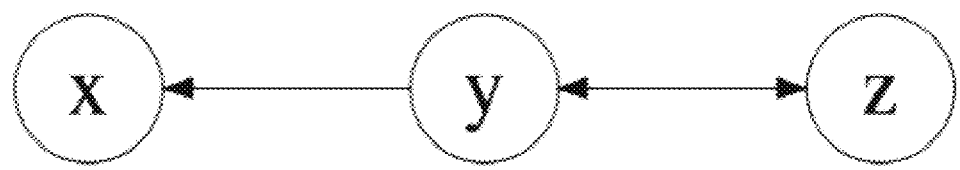
FIG. 5(a) illustrates a consistent joint structure.
Figure 5B:
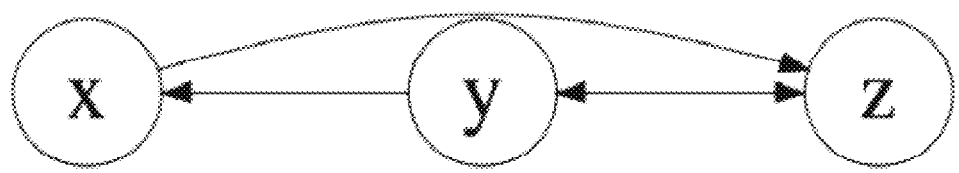
FIG. 5(b) illustrates a joint structure ruled out by causal sufficiency.

For instance, positing that X causes Z, as depicted in FIG. 5(b), leads to a direct cause from Y to Z—mediated by X—as well as the original common cause between Y and Z. That is, the structure is as depicted in FIG. 4(d) for appropriate node labels.

Figure 4C:
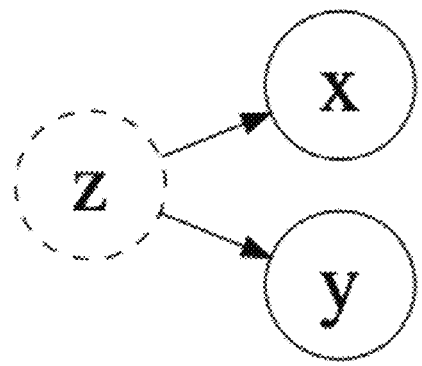
FIG. 4(c) is a possible causal structure between two correlated variables, solid nodes indicate observed variables and dashed nodes indicate latent variables.

However, this contradicts the original marginal structure, which detected only a common cause between Y and Z, as depicted in FIG. 4(c). As the algorithm used to learn this structure was promised to be causally sufficient, and hence can distinguish all structures in FIG. 4(a) to FIG. 4(e), we conclude that X cannot be a cause of Z. We can similarly conclude that Z cannot be a cause of X. Hence, neither joint causal structures in FIG. 5(b) and FIG. 5(c) are consistent with the marginal structures learned from each dataset.

Figure 5C:
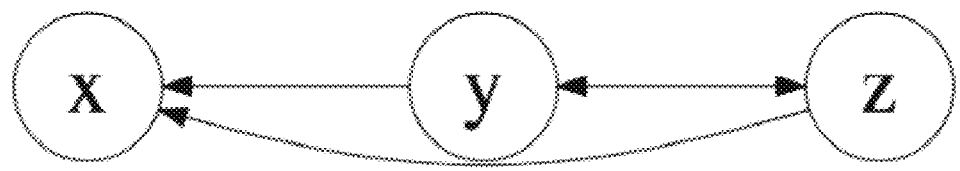
FIG. 5(c) illustrates a joint structure ruled out by causal sufficiency.

If previous approaches to learning consistent joint causal structures had been employed, such as ION and IOD, it would not be possible to rule out the structures in FIG. 5(b) and FIG. 5(c). Indeed, as ION and IOD employ conditional independence tests to discover underlying causal structure, they would not detect any contradiction between these joint structures and the marginal structures of each dataset. That is, due to the fact that all causal structures from FIG. 4(a) to FIG. 4(e) belong to the same Markov equivalence class, conditional independence tests cannot distinguish between directed causes and simultaneously direct-and-common causes. Hence, the ION and IOD algorithms output a larger set of consistent joint causal structures than the approach described above.

This example illustrates that exploiting causally sufficient bivariate causal discovery algorithms allows the output of a smaller solution set of joint causal structures consistent with individual datasets—thus getting closer to the true causal structure.

While the above example is for two datasets, each containing two variables, this example could be extended by any number of overlapping datasets, each having an arbitrary number of variables.

While there are many algorithms that can only distinguish between the causal structures in FIG. 4(a) and FIG. 4(b), there are a few bivariate causal discovery algorithms that are causally sufficient in their respective domains of applicability. Moreover, other bivariate causal discovery algorithms have had the robustness of their algorithms to unobserved confounding tested, showing they can in some instances detect the presence of latent common causes. Thus, the assumption of causal sufficiency is possible in some domains with current causal discovery algorithms. Additionally, expert knowledge and intervention-based studies can provide causally sufficient information.

For instance, in the above example, all that was needed for FIG. 5(b) to be ruled out was the knowledge that X could not be a mediator between Y and Z. In some domains, such as medicine, experts may provide such information. This knowledge could be used in conjunction with non-causally sufficient bivariate algorithms to achieve the same conclusions as reached above using causally sufficient algorithms. Additionally, as interventions decouple common cause influence, intervention-based studies can detect the presence of latent confounding and hence provide causally sufficient information.

Therefore, causally sufficient bivariate causal discovery greatly reduces the number of joint causal structures consistent with the causal information extracted from individual datasets. The reason is twofold. First, bivariate causal discovery algorithms allow us to determine the specific member of the Markov equivalence class the local datasets belong to. Second, the ability, given some assumptions, to distinguish all structures in FIG. 4(a) to FIG. 4(e) provides a richer set of conditions—beyond conditional independence—to check in order to ensure consistency. However, care should be taken when applying bivariate causal discovery to overlapping datasets. The identifiability requirements of such algorithms should hold under marginalisation for consistent application. Employing algorithms that do not make parametric assumptions is vital.

The method developed here assumes access to a causally sufficient bivariate causal discovery algorithm. This assumption is justified based on the following reasons: (1) future causal discovery algorithms may increase the domain in which causal sufficiency holds; (2) certain robustness tests for determining the presence of unobserved confounding are possible and (3) expert domain knowledge, such as provided by a medical professional, and intervention-based studies can also provide causally sufficient information. It is also assumed that all datasets come from the same underlying data generating process, as is done in IOD.

In an embodiment, a method is provided for faithfully storing such causally sufficient information, enabling the determination of whether potential joint causal structures are consistent with the marginal structures of each dataset.

A method is required for checking that a candidate MAG encodes the causal information learned from each dataset; that is, criteria is required that can distinguish each of the causal structures in FIG. 4(a) to FIG. 4(e). This is so that consistency of causal information between a candidate MAG and the MAGs of the individual datasets can be graphically checked. Motivated both by the manner in which the IOD algorithm stores graphical information about conditional independence using the two data structures, and also by Pearl's do-calculus rules, the criteria for distinguishing all causal structures from FIG. 4(a) to FIG. 4(e), of an embodiment, involves exploiting (in)dependence information in mutilated versions of the original MAG, which is now described. In the following, $(\ldots)_{\overline{Z}}$ denotes a condition in a MAG with incoming edges removed from node Z, and $(\ldots)_{\underline{Z}}$ denotes the same but with outgoing edges removed.

Criterion 1, FIG. 4(a): $(X \perp\!\!\!\perp Y)_{\overline{X}} (X \not\!\perp\!\!\!\perp Y)_{\underline{Y}} (X \not\!\perp\!\!\!\perp Y)_{\overline{X}} (X \perp\!\!\!\perp Y)_{\underline{X}}$ Criterion 2, FIG. 4(b): $(X \not\!\perp\!\!\!\perp Y)_{\overline{X}} (X \perp\!\!\!\perp Y)_{\underline{Y}} (X \perp\!\!\!\perp Y)_{\overline{X}} (X \not\!\perp\!\!\!\perp Y)_{\underline{X}}$ Criterion 3, FIG. 4(c): $(X \perp\!\!\!\perp Y)_{\overline{X}} (X \not\!\perp\!\!\!\perp Y)_{\underline{Y}} (X \perp\!\!\!\perp Y)_{\overline{X}} (X \not\!\perp\!\!\!\perp Y)_{\underline{X}}$ Criterion 4, FIG. 4(d): $(X \perp\!\!\!\perp Y)_{\overline{X}} (X \not\!\perp\!\!\!\perp Y)_{\underline{Y}} (X \not\!\perp\!\!\!\perp Y)_{\overline{X}} (X \not\!\perp\!\!\!\perp Y)_{\underline{X}}$ Criterion 5, FIG. 4(e): $(X \not\!\perp\!\!\!\perp Y)_{\overline{X}} (X \not\!\perp\!\!\!\perp Y)_{\underline{Y}} (X \not\!\perp\!\!\!\perp Y)_{\overline{X}} (X \not\!\perp\!\!\!\perp Y)_{\underline{X}}$ In FIG. 4(a), if the outgoing edge from X is removed, then there is no link between X and Y and they are hence independent variables in this new "mutilated" graphical model. There are no arrows coming out of Y, so X and Y are still connected and hence dependent in the "mutilated" graph were the arrows coming out of Y are dropped (there aren't any).

In FIG. 4(b), if the outgoing edge from Y is removed, then there is no link between X and Y and they are hence independent variables in this new "mutilated" graphical model. There are no arrows coming out of X, so X and Y are still connected and hence dependent in the "mutilated" graph were the arrows coming out of X, are dropped (there aren't any).

Hence, it is possible to distinguish between FIG. 4(a) to FIG. 4(e) by applying the above criterion.

For example, comparing Criterion 1 above with FIG. 4(a), it can be seen that checking $(X \perp\!\!\!\perp Y)_{\overline{X}}$ distinguishes FIG. 4(a) from the other structures of FIG. 4(b) to FIG. 4(e).

For example, comparing Criterion 3 above with FIG. 4(c), it can be seen that checking $(X \perp\!\!\!\perp Y)_{\overline{X}}$ and $(X \perp\!\!\!\perp Y)_{\overline{X}}$ distinguishes FIG. 4(c) from the other structures of FIG. 4(a), FIG. 4(b), FIG. 4(d) and FIG. 4(e).

These criterion provide a method for faithfully storing such causally sufficient information, allowing it to be easily determined if potential joint causal structures are consistent with the marginal structures of each dataset.

Taking the structure of FIG. 5 (a), a candidate MAG must satisfy criterion 3 for (Y,Z) and criterion 1 for (Y,X). FIG. 2 (b) violates criterion 3 for (Y,Z), as Y and Z are dependent when both their incoming edges are removed. FIG. 5 (c) violates criterion 1 for (Y,X), as Y and X are dependent when Y's outgoing edge is removed.

Given the above criterion, the method of generating a graphical model from multiple overlapping datasets proceeds as follows.

Starting from a fully connected, unorientated graph for each variable set $\langle \mathcal{G}_1 \ldots \mathcal{G}_n \rangle$, where the variable sets are denoted by $\langle \mathcal{V}_1 \ldots \mathcal{V}_n \rangle$, edges are dropped and immoralities orientated using conditional independence tests on each dataset. These processes are also carried out on a fully connected graph, $\mathcal{G}$, containing all the variables $\mathcal{V} = \cup_{i=1}^{n} \mathcal{V}_i$. Any conditional independence information, along with the conditioning set, are stored in a data structure Sepset. If two dependent variables from $\mathcal{V}_i$ are not conditionally independent given any other set of nodes, the pair is added, along with $\mathcal{V}_i$, to a data structure called IP. In reality this step accesses a set Possep to obtain the necessary independence information.

To improve the robustness of the independence tests across the datasets, the p-values of the tests for overlapping variables are pooled using Fisher's method. The output of this step is the partially unoriented graphs, a global graph, $\mathcal{G}, \mathcal{G}_1, \ldots \mathcal{G}_n$ and along with the data structures Sepset and IP.

Next, bivariate causal discovery is applied to each dataset, and the edges oriented accordingly in all the above graphs $\mathcal{G}, \mathcal{G}_1, \ldots \mathcal{G}_n$. The causal structure found between each pair of dependent variables is then stored in three new data structures—Directed((X,Y)) for FIG. 4(a) and FIG. 4(b), Common((X,Y)) for FIG. 4(c), and DirectedCommon((X, Y)) for FIG. 4(d) and FIG. 4(e). The order of the variables conveys the direction of the arrow in Directed((X,Y)) and DirectedCommon((X,Y)).

The global graph $\mathcal{G}$ now consists of a superset of edges and a subset of immoralities compared to the true data generating graph. This motivates the next step, which considers edges to remove in $\mathcal{G}$ and, within the resulting graph, immoralities to orient. Conditions for edges to remove and immoralities to orient are in R. Tillman and P. Spirtes, "Learning equivalence classes of acyclic models with latent and selection variables from multiple datasets with overlapping variables," in Proceedings of the Fourteenth International Conference on Artificial Intelligence and Statistics, pp. 3-15, 2011.

This step requires iteration over the powerset of edges to remove and, within it, iteration over the powerset of immoralities to orient. At each iteration $\mathcal{G}$ is converted to a PAG using the rules in Zhang (J. Zhang, "A characterization of markov equivalence classes for directed acyclic graphs with latent variables," in Proceedings of the Twenty-Third Conference on Uncertainty in Artificial Intelligence, UAI'07, (Arlington, Va., United States), pp. 450-457, AUAI Press, 2007), which finds all invariant tails and arrows.

The PAG is then converted to a MAG in its equivalence class and it is checked whether: (1) it is indeed a MAG, (2) m-separations in the MAG are consistent with those in Sepset and (3) there is an inducing path between every variable pair in IP with respect to $\mathcal{V} \setminus \mathcal{V}_i$. If a MAG satisfies all conditions, the corresponding PAG marginalises to the dataset PAGs, and is returned as a candidate for the true graphical structure.

The output of this step is a set of candidate solutions for the joint causal structure among all variables which are consistent with the conditional independences learned previously.

Figure 6:
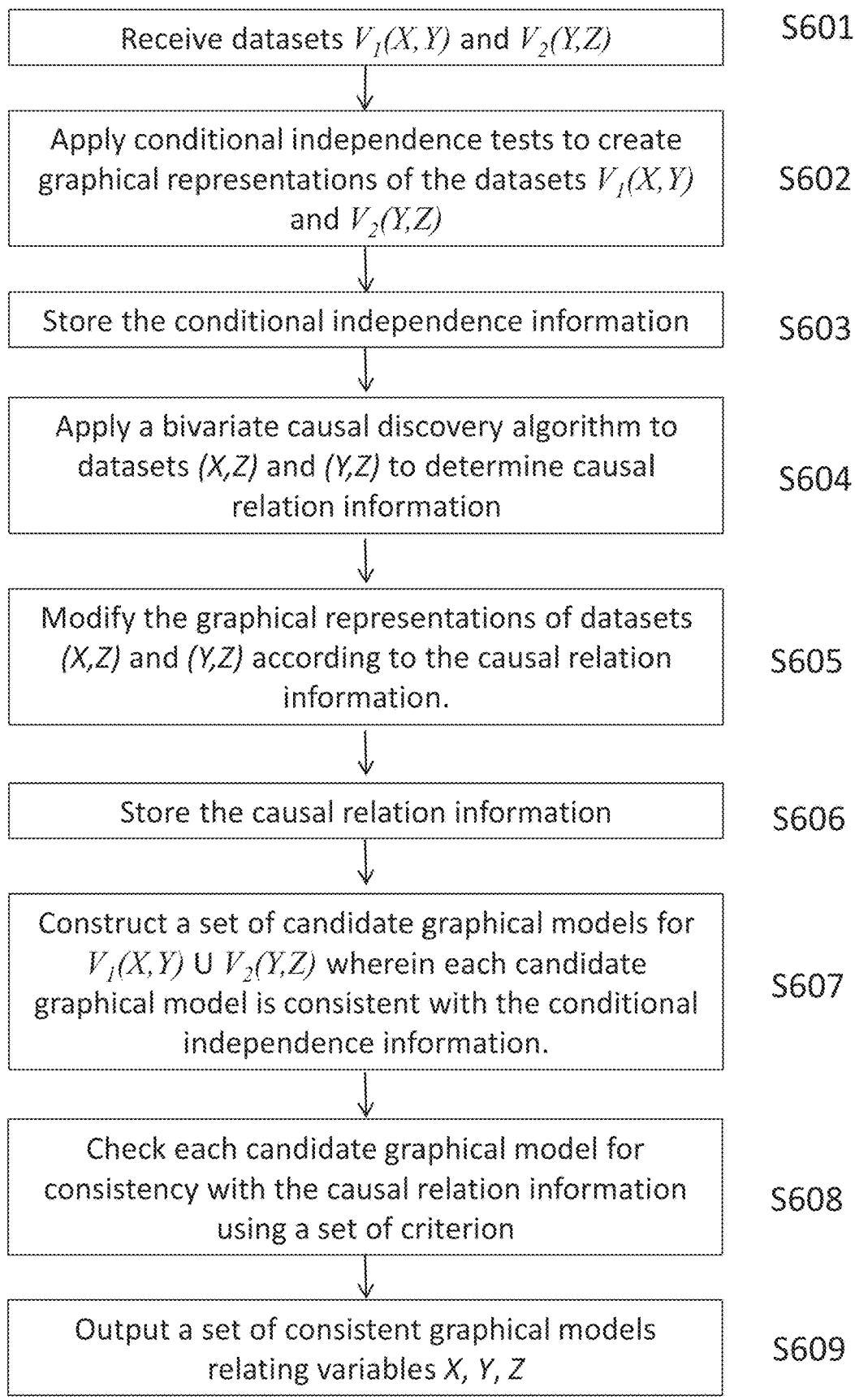
FIG. 6 is a flow chart depicting a method in accordance with an embodiment.

Finally, these candidate solutions are filtered for causal consistency by checking that each pair of variables in the data structures Directed((X,Y)), Common((X,Y)), and DirectedCommon((X,Y)) has the required causal structure in the candidate MAG. This is achieved by checking if the criterion relevant to the data structure holds in the MAG between the pair of variables. If the requisite criteria are satisfied for all the pairs of variables stored in the data structures, then the candidate graph is accepted as a consistent solution, otherwise it is discarded. This method is outlined as follows:

FIG. 6 illustrates how the steps of the method of creating a graphical representation are carried out.

In S601, multiple data sets are received, for example a first data set $\mathcal{V}_1$ and a second data set $\mathcal{V}_2$. The method enables these data sets to be fused in the creation of graphical models.

The first data set $\mathcal{V}_1$ comprises two variables, for example, $\mathcal{V}_1(X,Y)$. The second data set comprises two variables $\mathcal{V}_2(Y,Z)$. Therefore, the first data set and the second data set are overlapping in terms of the variable Y.

While FIG. 6 indicates data fusion for two datasets, each containing two variables, the method of FIG. 6 can be extended to any number of overlapping datasets, each having an arbitrary number of variables.

In S602, conditional independence tests are applied on the first data set $\mathcal{V}_1$ and the second data set $\mathcal{V}_2$. This allows for graphical models $\mathcal{G}_1$ and $\mathcal{G}_2$ of the first dataset $\mathcal{V}_1$ and the second dataset $\mathcal{V}_2$ to be created.

Starting from fully connected graphs $\mathcal{G}_1$ and $\mathcal{G}_2$ for each dataset $\mathcal{V}_1$ and $\mathcal{V}_2$, edges can be dropped and immoralities orientated using conditional independence tests on each dataset. These processes are also carried out on a fully connected graph $\mathcal{G}$ containing all the variables $\mathcal{V}$.

Following these processes, S602 returns graphs $\mathcal{G}$, $\mathcal{G}_1$ and $\mathcal{G}_2$.

In S603, any conditional independence information, along with the conditioning set, obtained during S602 are stored in a data structure Sepset. If there is no conditioning set between two nodes, the pair is added, along with the variables in the dataset $\mathcal{V}_i$, to another data structure called IP (This step accesses a set Possep to obtain the necessary independence information). To improve the robustness of the independence tests across the datasets, the p values of the tests for overlapping variables are pooled using Fisher's method. The output of this step is the data structures Sepset and IP which store conditional independence information.

In S604, a bivariate causal discovery algorithm C is applied to the first dataset $\mathcal{V}_1$ and the second dataset $\mathcal{V}_2$ to determine the causal relation between the variables {X,Y} in $\mathcal{V}_1$, and to determine the causal relation between the variables {Y,Z} in $\mathcal{V}_2$.

In S605, the edges in each graph $\mathcal{G}$, $\mathcal{G}_1$ and $\mathcal{G}_2$ are oriented according to the resulting causal structure.

In S606, the causal structure found between each pair of dependent variables is then stored. This may be in three new data structures—Directed({X,Y}) for FIG. 4(a) and FIG. 4(b), Common({X,Y}) for FIG. 4(c), and DirectedCommon({X,Y}) for FIG. 4(d) and FIG. 4(e). The order of the variables conveys the direction of the arrow in Directed({X,Y}) and DirectedCommon({X,Y}) structures.

In S607, candidate solutions for the joint causal structure among all variables (X,Y,Z), which are consistent with the conditional independence information learned in S602 are obtained from graphs $\mathcal{G}$, $\mathcal{G}_1$ and $\mathcal{G}_2$. In other words, this step finds all the graphical representations for the union of datasets $\mathcal{V}_1$ and $\mathcal{V}_2$, i.e. $\mathcal{V}_1(X,Y) \cup \mathcal{V}_2(Y,Z)$ that don't contradict the conditional independence information stored in S603. The global graph $\mathcal{G}$ now consists of a superset of edges and a subset of immoralities compared to the true data generating graph. This motivates the next step, which considers edges to remove in $\mathcal{G}$ and, within the resulting graph, immoralities to orient. Conditions for edges to remove and immoralities to orient are in R. Tillman and P. Spirtes, "Learning equivalence classes of acyclic models with latent and selection variables from multiple datasets with overlapping variables," in Proceedings of the Fourteenth International Conference on Artificial Intelligence and Statistics, pp. 3-15, 2011.

This step requires iteration over the powerset of edges to remove and, within it, iteration over the powerset of immoralities to orient. At each iteration $\mathcal{G}$ is converted to a PAG using the rules in Zhang (J. Zhang, "A characterization of markov equivalence classes for directed acyclic graphs with latent variables," in Proceedings of the Twenty-Third Conference on Uncertainty in Artificial Intelligence, UAI'07, (Arlington, Va., United States), pp. 450-457, AUAI Press, 2007), which finds all invariant tails and arrows.

The PAG is then converted to a MAG in its equivalence class and it is checked whether: (1) It is indeed a MAG, (2) m-separations in the MAG are consistent with those in Sepset, and (3) there is an inducing path between every variable pair in IP with respect to $\mathcal{V} \setminus \mathcal{V}_i$. If a MAG satisfies all conditions, the corresponding PAG marginalises to the dataset PAGs, and is returned as a candidate for the true graphical structure.

In S608, the candidate graphical representations are filtered for causal consistency by checking that the causal relation information stored for each pair of variables in S606 has the required causal structure in the candidate MAG.

This is achieved by checking if the criterion relevant to the data structure holds in the MAG between the pair of variables. If the requisite criteria are satisfied for all the pairs of variables stored in the data structures, then the candidate graph is accepted as a consistent solution, otherwise it is discarded.

This is repeated on every possible MAG in PAGs generated in S607.

The output of the method, as shown in S609, is consistent PAGs (if every MAG is consistent) and consistent individual MAGs.

The result of the method is that all those graphical models, which contradict the information stored in the causal relation information are thrown away, resulting in a smaller set of graphical representations for the union of datasets.

As an example, at S604, suppose the bivariate causal discovery algorithm determined that X was caused by Y, i.e. X←Y, and that Y and Z share a latent common cause, i.e. Y↔Z. This causal relation information is stored in S606.

Suppose, FIG. 5(a) is a candidate graphical representation, constructed in S607, from the datasets $\mathcal{V}_1(X,Y)$ and $\mathcal{V}_2(Y,Z)$. In S608, the criterion 1-5 are applied to FIG. 5(a) for each pair of variables.

For example, the criterion 1-5 are applied first for variables (X,Y). The graph of FIG. 5(a) will uphold Criterion 2, but will violate Criterion 1 and Criterion 3 to 5 with respect to the variables (X,Y).

Thus the structure between X and Y has been identified as that in FIG. 4(b).

The criterion 1-5 are applied to the candidate graphical representation FIG. 5(a) for variables (Y,Z). In this case, the graph of FIG. 5(a) will uphold Criterion 3, but will violate Criterion 1, 2, 4 and 5 with respect to the variables (Y,Z).

Thus the structure between Y and Z has been identified as that in FIG. 4(c).

The identified structure for (X,Y) and (Y,Z) are then checked with the stored causal relation information by determining whether the criterion relevant to the data structure holds in the MAG between the pair of variables.

If the above identified structures contradict the stored causal relation information for any of the pairs of variables, then the candidate graphical representation is discarded.

However, in the case of FIG. 5(a), there is no contradiction between the identified structures and the stored causal information X←Y and Y↔Z. Thus, FIG. 5(a) is kept.

Suppose, FIG. 5(b) is another candidate graphical representation, constructed in S607. In S608, the criterion 1-5 are applied to FIG. 5(b) for each pair of variables.

For example, the criterion 1-5 are applied first for variables (X,Y). The graph of FIG. 5(b) will uphold Criterion 2 with respect to the variables (X,Y).

Thus the structure between X and Y has been identified as that in FIG. 4(b).

The criterion 1-5 are applied to the candidate graphical representation FIG. 5(b) for variables (Y,Z). In this case, the graph of FIG. 5(b) will uphold Criterion 4, but will violate Criterion 1, 2, 3 and 5 with respect to the variables (Y,Z).

Thus the structure between Y and Z has been identified as that in FIG. 4(d).

The identified structures for (X,Y) and (Y,Z) are then checked with the stored causal relation information by determining whether the criterion relevant to the data structure holds in the MAG between the pair of variables.

However, as Criterion 3 for variables (Y,Z) has been violated (Y and Z are dependent when both their incoming edges are removed) this contradicts the causal relation information which only identified a common cause between Y and Z. Thus, the candidate graphical representation of FIG. 5(b) is discarded.

Similarly, suppose FIG. 5(c) is another candidate graphical representation, constructed in S607. Then during the method FIG. 5(c) would be discarded as it violates criterion 1 for (X,Y), as Y and X are dependent when Y's outgoing edge is removed.

Therefore, in this example, the set of consistent graphs output would comprise of FIG. 5(a) only.

The above method enables the combination and compilation of multiple overlapping datasets into a graphical model that then indicates relations between variables that were never measured together. The smallest set of consistent causal relations between variables in different datasets that were never jointly measured can be learned, as long as those datasets do have some variables in common.

The above method results in a smaller set of graphical representations for the union of datasets than using other methods. Thus, it provides an improved method of determining the true graphical model relating overlapping datasets, as the true graphical model is contained within the set of consistent graphical representations. Using this set, it may be determined what extra data is needed in order to obtain the true model.

The output of the above method is a selection of graphical representations. For example, if one dataset related smoking to high blood pressure, and another related diabetes to high blood pressure, the above method would provide a set of graphical models relating smoking, blood pressure and diabetes. Ultimately, these models could be used for diagnosis or triage, as illustrated in FIG. 7.

By combining multiple overlapping datasets, as outlined in the method of FIG. 6, into a graphical structure, inference can be performed on the resulting model. This model can be used for diagnosis or triage.

Figure 7:
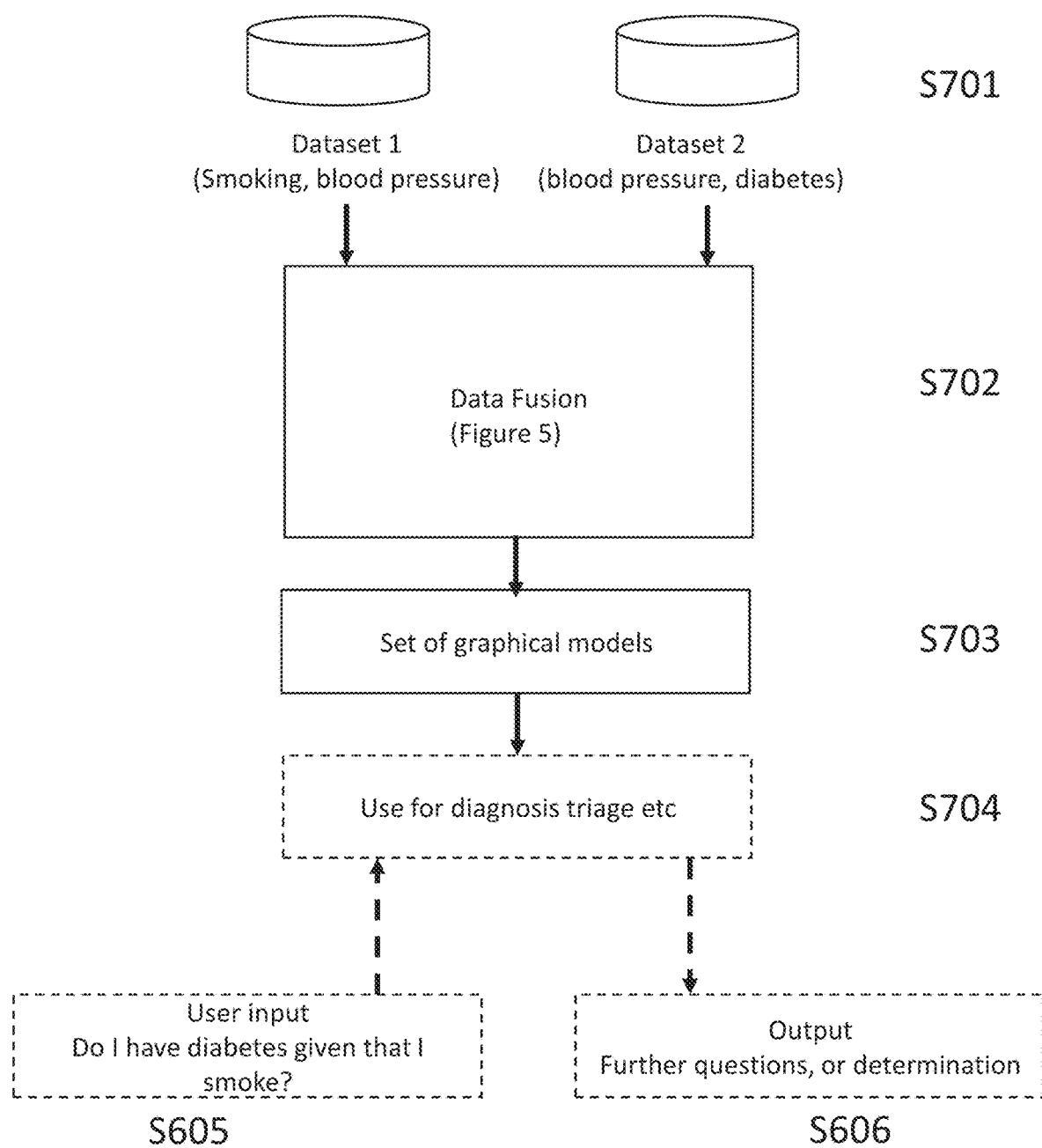
FIG. 7 is a schematic of a system in accordance with an embodiment.

In FIG. 7, dataset 1 and dataset 2 are provided at S701. Dataset 1 relates the variables smoking and blood pressure. Dataset 2 relates the variables blood pressure and diabetes.

While FIG. 7 indicates data fusion for two datasets, each containing two variables, the method of FIG. 7 can be extended to any number of overlapping datasets, each having an arbitrary number of variables.

In S702, both dataset 1 and dataset 2 are fused using the method of FIG. 6.

In S703, a set of graphical models is generated, wherein each model relates the variables smoking, blood pressure and diabetes.

In S704, these models are used in computer-implemented diagnosis or triage. In one embodiment, a single graphical model might be selected for use in the diagnosis or triage. For example, a medical expert can choose between the graphical models to select the one best reflecting the medical ground truth.

On receiving the user input at S705, a node in the model may be identified. Inference may then be performed on the model to provide a response to the user input at S706. The response may be a determination, a diagnosis or a list of further questions. For, example, this can be as described with reference to FIG. 8.

Figure 8:
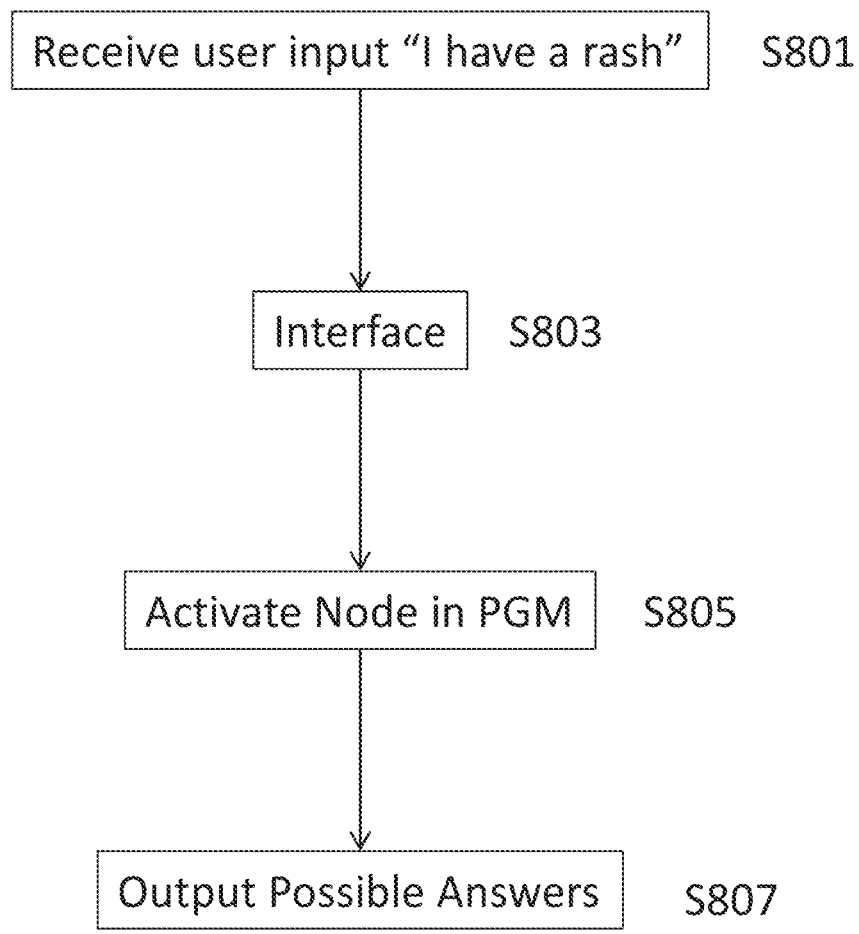
FIG. 8 is a flow chart in accordance with an embodiment, showing a dialogue supported by a graphical generated as described in FIG. 5.

In step S801 of FIG. 8, the user inputs the phrase, for example, "I have a rash" into, for example, the mobile telephone of FIG. 1. This phrase is then passed to the interface S803 that is used to identify a node in the PGM that relates to the user's query.

The node in the PGM is activated in step S805. The PGM is built using the method described with reference to FIGS. 6 to 7. Once an evidence node has been activated in the PGM, Bayesian inference can then be performed to output possible causes in step S807 for the user's symptoms or further questions that will allow the possible causes for the user's symptoms to be narrowed.

The above method combines multiple overlapping datasets into a graphical structure. The resulting graphical model requires less computing memory and storage than storing the datasets individually. Thus, the above method improves computational storage requirements and efficiency. Further, the described method improves the computational efficiency in performing inference on multiple datasets.

The above method is sound in that each returned MAG has the same marginal structure between variables as that learned from the datasets, and complete in that if a MAG exists with the same marginal structure between all variables, then it is returned by the method of FIG. 6.

Theorem 1 (Soundness).

Let $V_i, V_j \in D_k$ be variables in the overlapping dataset $D_k$. If the marginal causal structure between $V_i, V_j$ learned from $D_k$ is FIG. 4 (a), 4 (b), 4 (c), 4 (d), or 4 (e), then it is also the marginal structure between $V_i, V_j$ in every MAG output by the method of FIG. 5, for all i,j,k.

Proof of Theorem 1.

First, all MAGs output have the same conditional independence information as learned from $\mathcal{D} = \{D_1, \ldots, D_n\}$. All that remains to check is whether a solution output by the method of FIG. 5 has the same marginal causal structure between each pair of jointly measured variables as learned from $\mathcal{D}$. The only situations that pose a potential problem are structures that are initial purely directed (FIG. 4(a) or FIG. 4(b)) or common cause (FIG. 4(c)), as they could become simultaneous direct and common (FIG. 4(d) or FIG. 4(e)) when causal connections between non-jointly measured variables are added. However, as criterion 1-5 can distinguish between all of these cases, this problem does not arise.

Theorem 2 (Completeness).

Let $\mathcal{H}$ be a MAG over variables $D_k$. If $V_i, V_j \in_{k\ k}$ for some k and the marginalised causal structure between $V_i, V_j$ in $\mathcal{H}$ coincides with that learned from $D_k$, then $\mathcal{H}$ is one of the MAGs output by the method of FIG. 5.

Proof of Theorem 2.

First, all PAGs with the same conditional independence information as $\{D_1, \ldots, D_n\}$ are output by IOD. Note also that applying bivariate causal discovery to a MAG does not change the Markov equivalence class it belongs to. The conjunction of these two facts implies the method of FIG. 5 is complete.

Experiments

Results of experiments to compare the above method (referred to as Method 1) to normal IOD are presented. Additionally, to determine whether criteria 1-5 offer improvement over a straightforward application of bivariate causal discovery in the method, a comparison of the performance of the above method 1 to a modified version of method of FIG. 6 in which S606, S608 and S609 were omitted. This is referred to as Method 2. IOD struggles when both the number of overlapping variables and the number of variables in each individual dataset are small. Therefore, the methods are tested in this challenging regime. All three methods are compared on two synthetic examples and two real examples involving protein and breast cancer data. Also, in order to assess how performance varies across all algorithms as a function of overlap size, the methods are compared on randomly generated graphs where the number of overlapping variables is varied.

Figure 13:
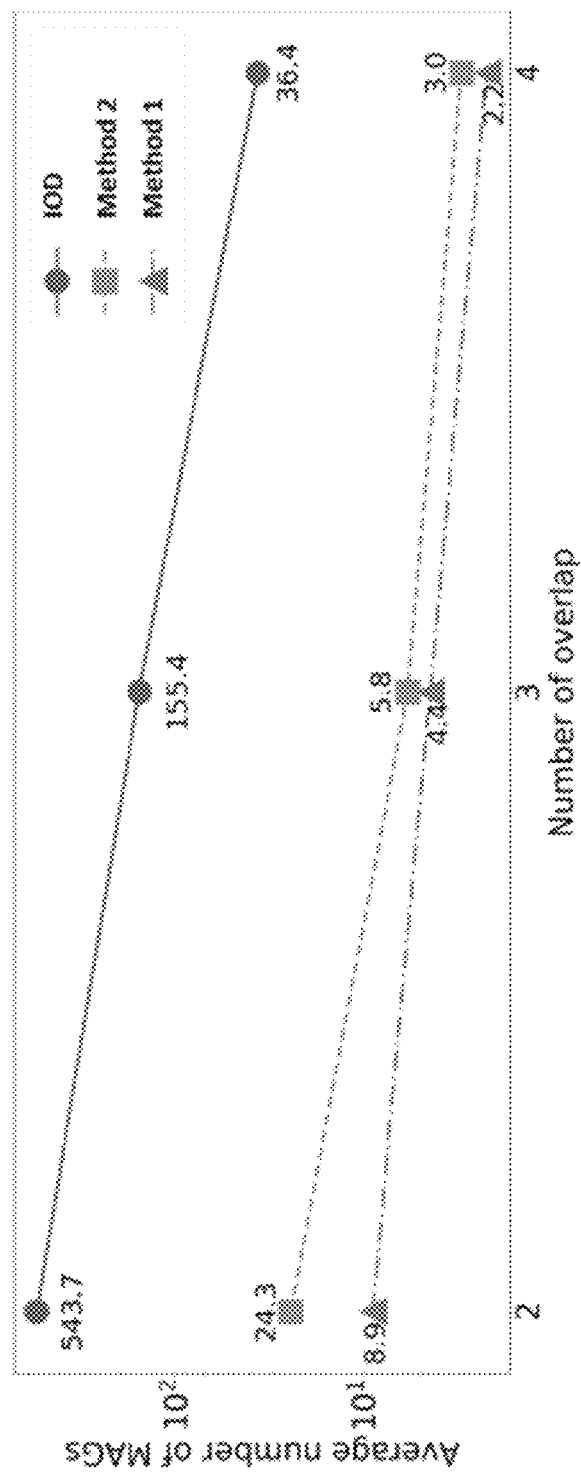
FIG. 13 shows average output of the algorithms on random graphs as a function of overlap variables.

The partition of variables in the two synthetic examples were chosen so that the local graphs satisfy causal sufficiency. This was done in order to compare performance when criteria 1-5 can be safely applied. General non-linear functions with multiplicative exponential noise were used to sample from synthetic graphical structures, with sample size 3000. Unless otherwise mentioned, independence tests HSIC and KCIT were used alongside the causal discovery algorithm KCDC to construct the local graphs. The above methods used the RBF kernel with median data distance as the scale. In the overlap and real-world protein examples, it was wished to attribute any difference in performance to both the incorporation of bivariate causal information and to criteria 1-5, rather than any difference in implementation of bivariate causal discovery algorithm or conditional independence test. Thus, all three methods were given access to the ground truth graph in place of causal discovery and conditional independence tests in these two examples. Results are presented in FIG. 12 and FIG. 13.

Figure 9A:
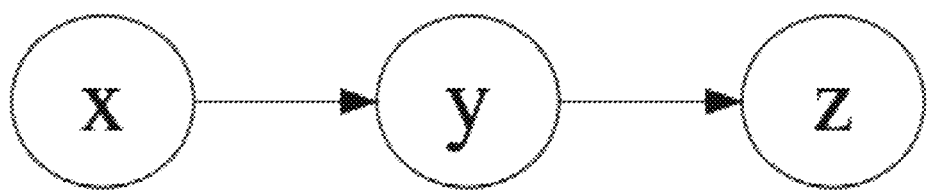
FIG. 9(a) illustrates the true graph for Synthetic 1.
Figure 9B:
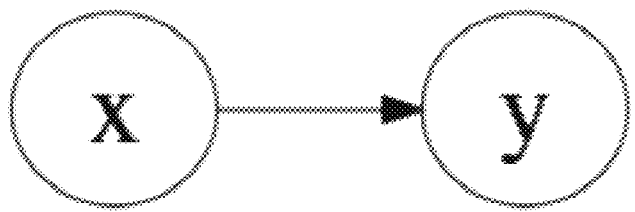
FIG. 9(b) illustrates a local graph after applying BCD.
Figure 9C:
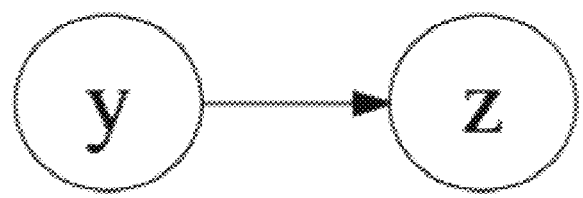
FIG. 9(c) illustrates a local graph after applying BCD.

Synthetic 1:

Data is sampled from the graphical structure depicted in FIG. 9(a). Here, the local datasets consist of the variables {X, Y} and {Y, Z}. FIG. 9(b) and FIG. 9(c) are the results of step 2 of algorithm 1 or S605 from FIG. 6. Note that without the bivariate causal discovery it would only be known that there was correlation among the variables, but it would not be possible to orient the causal direction. The number of consistent PAGs and, consequently, the number of consistent MAGs, are shown in the table of FIG. 12. The normal IOD in this case gives nearly every possible graphical structure between the three variables. This is because the conditional dependence information here will accept any graph between the three variables that results in a correlation between X,Y and Y,Z. Method 2 reduces the number of equivalence classes and the number of MAGs in each equivalence class. This is due to the fact that, as a consequence of the arrows being oriented, certain immoralities can be ruled out. Method 1 performs the best as any relationship between X and Z is instantly ruled out by the fact that it would invalidate the local causal information that X, Y and Y, Z have a directed cause.

Figure 10A:
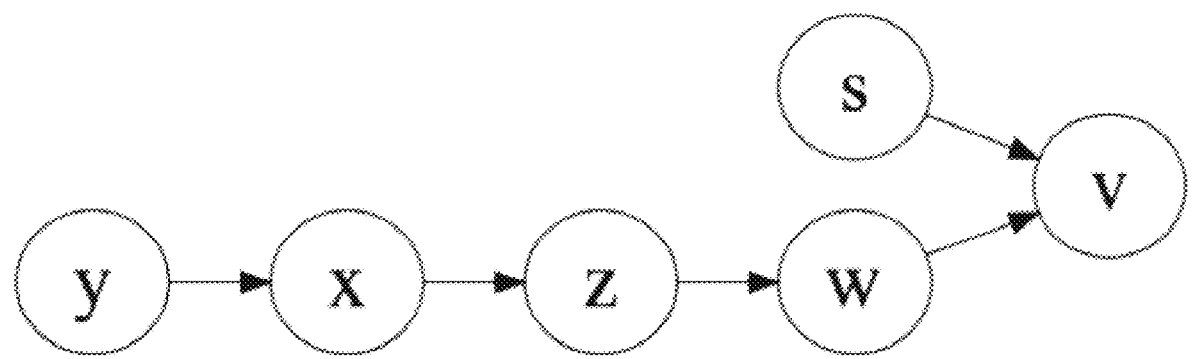
FIG. 10(a) illustrates the true graph for Synthetic 2.
Figure 10B:
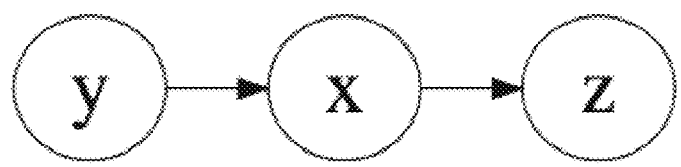
FIG. 10(b) illustrates a local graph after applying BCD.
Figure 10C:
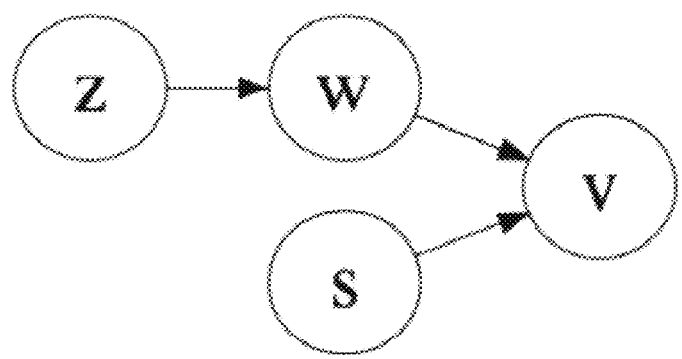
FIG. 10(c) illustrates a local graph after applying BCD.
Figure 11A:
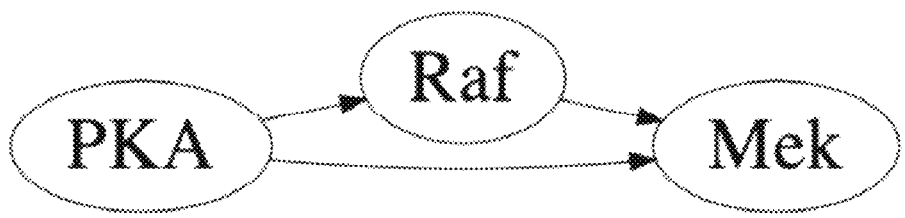
FIG. 11(a) illustrates a local causal graph of the Protein dataset.
Figure 11B:
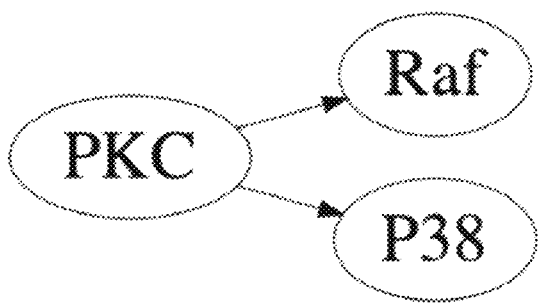
FIG. 11(b) illustrates a local causal graph of the Protein dataset.
Figure 11C:
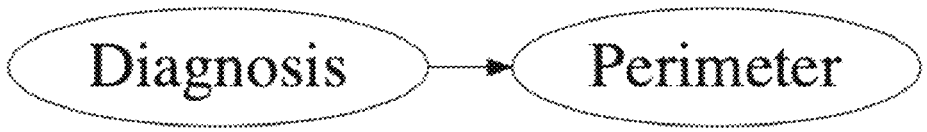
FIG. 11(c) illustrates a local causal graph of the Cancer dataset.
Figure 11D:
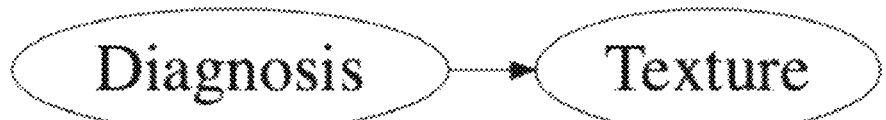
FIG. 11(d) illustrates a local causal graph of the Cancer dataset.

Synthetic 2:

Data is generated from a model whose graphical structure is depicted in FIG. 10(a). Here, the normal IOD was not compared to Method 1 and Method 2, as its computation proved intractable. The reason for this was the fact that the small overlap in this case created too many edges to remove and immoralities to orient (first iteration is over the powerset of a list of length 29). As the bivariate causal discovery orients the edges in the local graphs, it substantially reduces the number of immoralities to consider. This saves considerable compute time. The results in the table of FIG. 12 show that Method 1 returns the correct graph while Method 2 results in multiple consistent answers. The reason Method 1 performs well is again due to the fact that Y,X,Z have a pairwise directed cause among them, as seen in FIG. 10 (b). This then rules out any graph that allows for a backdoor path between these variables, even if the graph respects the conditional independences of the datasets. This is also true of the variables in FIG. 10(c).

Overlap Experiment:

The three methods are compared on randomly generated graphs of 6 nodes created using the process described in G. Melancon, I. Dutour, and M. Bousquet-Me'lou, "Random generation of DAGs for graph drawing," 2000. Here, the number of overlap variables is varied and the number of resulting consistent MAGs is counted. The choice of overlap variables was fixed before the graph generation to ensure that the overlap was random. The global graph was generated and then marginalised into two separate local graphs. This is repeated with 20 random graphs, with the results averaged. The results of this can be seen in FIG. 13. Using causal information vastly decreases the number of consistent answers as the number of overlapping variables increases.

Protein:

Next, the algorithms are compared on the Sachs et al. protein dataset (K. Sachs, O. Perez, D. Pe'er, D. Lauffenburger, and G. Nolan, "Causal protein-signaling networks derived from multiparameter single-cell data," Science (New York, N.Y.), vol. 308, no. 5721, p. 523, 2005). Here, Sachs et al. perturbed different proteins, observing the responses of other proteins. A subset of variables and their causal connection are taken from the ground truth in Sachs et al. FIG. 11 (a)-(b) shows the variables chosen in the local dataset, as well as the causal connections. Normal IOD was again intractable here (first iteration of immoralities was over the powerset of a list of length 24).

Breast Cancer:

The method was also tested on the Breast Cancer dataset. This dataset contains 10 features that describe the cell nucleus present in the image of a breast mass. The images are associated with a diagnoses of breast cancer (Malignant or Benign). Three variables—Diagnosis, Perimeter, & Texture—were chosen and partitioned into two datasets with Diagnosis as the overlapping variable, as in FIG. 101 (c)-(d). One might argue that causal sufficiency could be assumed here as we do not expect the Diagnosis and a physical feature to be confounded by the other physical feature. However, Method 1 and Method 2 yield the same answers here, hence criteria 1-5 provide no advantage in this case.

The new sound and complete method for discovering causal structure from multiple overlapping datasets using bivariate causal discovery has been disclosed herein. This method outperformed the current state-of-the-art algorithm, IOD—even when both the number of overlapping variables and the number of variables in each individual dataset were small.

While it will be appreciated that the above embodiments are applicable to any computing system, an example computing system is illustrated in FIG. 14, which provides means capable of putting an embodiment, as described herein, into effect. As illustrated, the computing system 1200 comprises a processor 1201 coupled to a mass storage unit 1202 and accessing a working memory 1203. As illustrated, a graphical model 1206 obtained by the described method is represented as software products stored in working memory 1203. However, it will be appreciated that elements of the graphical model 1206 described previously, may, for convenience, be stored in the mass storage unit 1202.

Depending on the use, the graphical model 1206 may be used with a chatbot, to provide a response to a user question.

Usual procedures for the loading of software into memory and the storage of data in the mass storage unit 1202 apply. The processor 1201 also accesses, via bus 1204, an input/output interface 1205 that is configured to receive data from and output data to an external system (e.g. an external network or a user input or output device). The input/output interface 1205 may be a single component or may be divided into a separate input interface and a separate output interface.

Thus, execution of the graphical model 1206 by the processor 1201 will cause embodiments as described herein to be implemented.

The graphical model 1206 can be embedded in original equipment or can be provided, as a whole or in part, after manufacture. For instance, graphical model 1206 can be introduced, as a whole, as a computer program product, which may be in the form of a download, or to be introduced via a computer program storage medium, such as an optical disk. Alternatively, modifications to existing causal discovery model software can be made by an update, or plug-in, to provide features of the above described embodiment.

The computing system 1200 may be an end-user system that receives inputs from a user (e.g. via a keyboard) and retrieves a response to a query using the graphical model 1206 adapted to produce the user query in a suitable form. Alternatively, the system may be a server that receives input over a network and determines a response. Either way, the use of the graphical model 1206 may be used to determine appropriate responses to user queries, as discussed with regard to FIG. 1 and FIG. 7.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

In the above embodiments, a purely directed causal discovery algorithm is converted into one that can also detect latent common causes. The modified algorithm is tested extensively on synthetic and real datasets. In the experiments explained above, the modified algorithm maintained the performance of the original algorithm on the directed datasets and allowed algorithms that originally could not detect latent causes to uncover them in both synthetic and real data.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of methods and systems described herein may be made without departing from the spirit of the inventions. The accompanying claims and their equivalents are intended to cover such forms of modifications as would fall within the scope and spirit of the inventions.

The invention claimed is:

1. A computer implemented method of creating a model that is a graphical representation comprising:
   receiving a first dataset comprising a first variable and a third variable and a second dataset comprising a second variable and the third variable, wherein the first dataset and second dataset are overlapping in the third variable, wherein the first dataset and second dataset were not measured at the same time;
   creating graphical representations of the first dataset and the second dataset by applying conditional independence tests on the first dataset and second dataset;
   storing conditional independence information obtained by applying the conditional independence tests on the first dataset and the second dataset;
   applying a bivariate causal discovery algorithm to determine a causal relation between the first and third variable in the first dataset and a causal relation between the second and third variable in the second dataset, the causal discovery algorithm being able to determine if the first variable causes the third variable, the third variable causes the first variable, the second variable causes the third variable and the third variable causes the second variable;
   modifying the graphical representations of the first and second dataset according to the determined causal relations; and
   creating a set of candidate graphical representations for a third dataset comprising the first dataset and the second dataset, wherein each candidate graphical representation indicates a causal relationship between the first variable and the second variable, wherein each candidate graphical representation is consistent with the conditional independence information.

2. A method according to claim 1, wherein the bivariate causal discovery algorithm is causally sufficient, the method further comprising:
   storing causal relation information between pairs of variables, the causal relation information obtained by applying the bivariate causal discovery algorithm;
   checking each candidate graphical representation for consistency with the causal relation information using a set of criteria; and
   outputting a set of consistent graphical representations comprising candidate graphical representations that are consistent with the causal relation information.

3. A method according to claim 2 wherein the set of criteria distinguishes between possible causal structures between two variables in each candidate graphical representation.

4. A method according to claim 3 wherein checking each candidate's graphical representation for consistency with the causal relation information using a set of criteria comprises:
   applying the criteria to the candidate graphical representation to identify a causal structure between two variables;
   checking if the causal structure is consistent for the causal relation information for two variables.

5. A method according to claim 2 wherein the set of criteria encodes conditional independence information between variables in a causal structure.

6. A method according to claim 2 wherein the causal relation information is stored in three data structures depending on whether the relation between two variables is directed, comprises a common latent variable, or has both a directed relation and a common latent variable.

7. A method according to claim 2 wherein if the relation between the variables is a directed relation, the variables are stored in the data structure in an order that reflects the direction of the relation.

8. A method according to claim 2 wherein the set of consistent graphical representations comprises maximal ancestral graphs.

9. A method according to claim 2 wherein, if every maximal ancestral graph of a partial ancestral graph is consistent, the set of consistent graphical representations comprises the partial ancestral graph.

10. A non-transitory carrier medium carrying computer readable instructions being adapted to cause a computer to run the method recited in claim 1.

11. A computer-implemented method of determining a response to a user inputted query, using a model, the method comprising:
    receiving a user inputted query;
    identifying a node in said model related to said query, said model being stored in a memory of a computer; and
    performing inference on said model to provide a response to said user, wherein, said model is constructed by the method of claim 1.

12. A system adapted to generate a model that is a graphical representation, the system comprising a processor and a memory, the processor being adapted to:
    receive a first dataset comprising a first variable and a third variable and a second dataset comprising a second variable and the third variable, wherein the first dataset and second dataset are overlapping in the third variable, wherein the first dataset and second dataset were not measured at the same time;
    create graphical representations of the first dataset and the second dataset by applying conditional independence tests on the first dataset and second dataset;
    store conditional independence information obtained by applying the conditional independence tests on the first dataset and the second dataset;
    apply a bivariate causal discovery algorithm to determine a causal relation between the first and third variable in the first dataset and a causal relation between the second and third variable in the second dataset, the causal discovery algorithm being able to determine if the first variable causes the third variable, the third variable causes the first variable, the second variable causes the third variable and the third variable causes the second variable;
    modify the graphical representations of the first and second dataset according to the determined causal relations; and
    create a set of candidate graphical representations for a third dataset comprising the first dataset and the second dataset, wherein each candidate graphical representation indicates a causal relationship between the first variable and the second variable, wherein each candidate graphical representation is consistent with the conditional independence information.

13. A system according to claim 12, wherein the bivariate causal discovery algorithm is causally sufficient, the processor being further adapted to:

store causal relation information between pairs of variables, the causal relation information obtained by applying the bivariate causal discovery algorithm;
check each candidate graphical representation for consistency with the causal relation information using a set of criterion; and
output a set of consistent graphical representations comprising candidate graphical representations that are consistent with the causal relation information.

* * * * *